US012774308B2

(12) United States Patent
Timko et al.

(10) Patent No.: US 12,774,308 B2
(45) **Date of Patent: *Oct. 27, 2026**

(54) COMPOSITIONS AND RELATED METHODS FOR MODULATING ALKALOID PRODUCTION BY CONTROLLING PMT PROMOTER ACTIVATION MEDIATED BY TRANSCRIPTIONAL FACTORS ERF AND Myc

(71) Applicant: University of Virginia Patent Foundation, Charlottesville, VA (US)

(72) Inventors: Michael Paul Timko, Charlottesville, VA (US); Paul J. Rushton, Brookings, SD (US); Sheng-Cheng Han, Charlottesville, VA (US); Hongbo Zhang, Chongging (CN); Marta Tatiana Bokowiec, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 177 days.

This patent is subject to a terminal disclaimer.

(21) Appl. No.: 18/754,305

(22) Filed: Jun. 26, 2024

(65) Prior Publication Data

US 2024/0336662 A1 Oct. 10, 2024

Related U.S. Application Data

(60) Continuation of application No. 18/363,120, filed on Aug. 1, 2023, now Pat. No. 12,054,523, which is a continuation of application No. 17/517,305, filed on Nov. 2, 2021, now Pat. No. 11,760,781, which is a continuation of application No. 16/369,614, filed on Mar. 29, 2019, now Pat. No. 11,168,118, which is a continuation of application No. 15/644,199, filed on Jul. 7, 2017, now Pat. No. 10,280,203, which is a division of application No. 14/311,684, filed on Jun. 23, 2014, now Pat. No. 9,701,978, which is a continuation of application No. 12/676,871, filed as application No. PCT/US2008/010447 on Sep. 5, 2008, now Pat. No. 8,759,101.

(60) Provisional application No. 60/935,947, filed on Sep. 7, 2007, provisional application No. 60/935,948, filed on Sep. 7, 2007.

(51) Int. Cl.
*C12N 15/82* (2006.01)
*C07K 14/415* (2006.01)

(52) U.S. Cl.
CPC ........ *C07K 14/415* (2013.01); *C12N 15/8243* (2013.01)

(58) Field of Classification Search
None
See application file for complete search history.

(56) References Cited

U.S. PATENT DOCUMENTS

| | | | | |
|---|---|---|---|---|
| 8,624,083 | B2 * | 1/2014 | Page | A24B 15/12 435/6.12 |
| 8,759,101 | B2 * | 6/2014 | Timko | C07K 14/415 800/317.3 |
| 9,157,089 | B2 | 10/2015 | Page et al. | |
| 9,701,978 | B2 * | 7/2017 | Timko | C07K 14/415 |
| 2006/0041962 | A1 | 2/2006 | Inze et al. | |

FOREIGN PATENT DOCUMENTS

| | | | |
|---|---|---|---|
| WO | WO 2000/067558 | A1 | 11/2000 |
| WO | WO 2008/063203 | A2 | 5/2008 |

OTHER PUBLICATIONS

Altschul et al., "Basic local alignment search tool," *Journal of Molecular Biology*, 215(3): 403-410 (1990).
Altschul et al., "[27] Local alignment statistics," *Methods in Enzymology*, 266:460-480 (1996).
Corpet, "Multiple sequence alignment with hierarchical clustering," *Nucleic Acids Research*, 16(22): 10881-10890 (1988).
De Boer et al., "APETALA2/Ethylene Response Factor and basic helix-loop-helix tobacco transcription factors cooperatively mediate jasmonate-elicited nicotine biosynthesis," *The Plant Journal*, 66(6):1053-1065 (2011).
Elbashir et al., "Duplexes of 21-nucleotide RNAs mediate RNA interference in cultured mammalian cells," *Nature*, 411:494-498 (2001).
EMBL submission AJ630505.1 Mar. 9, 2004. [retrieved on Apr. 23, 2009] Retrieved from the internet :<URL: http://www.ebi.ac.uk/cgi-bin/emblfetch?style=html&id=AJ630505&Submit=Go>.
Fischer et al., "Overexpression of NtERF5, a New Member of the Tobacco Ethylene Response Transcription Factor Family Enhances Resistance to Tobacco mosaic virus," *Molecular Plant-Microbe Interactions*, 17(10):1162-1171 (2004).
GenBank Accession No. ET041915, "CHO_OF079xe23f1.ab1 CHO_OF Nicotiana tabacum genomic 5', genomic survey sequence," Oct. 12, 2007. [retrieved on May 4, 2022] Retrieved from the internet: <URL: https://www.ncbi.nlm.nih.gov/nuccore/ET041915>.
GenBank Accession No. ET047397, "CHO_OF4606xf16f1.ab1 CHO_OF4 Nicotiana tabacum genomic 5', genomic survey sequence," Oct. 12, 2007. [retrieved on May 4, 2022] Retrieved from the internet: <URL:https://www.ncbi.nlm.nih.gov/nuccore/ET047397>.
GenBank Accession No. ET047398, CHO_OF4606xf16r1.ab1 CHO_OF4 Nicotiana tabacum genomic 3', genomic survey sequence, Oct. 12, 2007. [retrieved on May 4, 2022] Retrieved from the internet: <URL:https://www.ncbi.nlm.nih.gov/nuccore/ET047398>.
GenBank Accession No. ET047429, "CHO_OF4609xb08r1.ab1 CHO_OF4 Nicotiana tabacum genomic 3', genomic survey sequence," Oct. 12, 2007. [retrieved on May 4, 2022] Retrieved from the internet: <URL:https://www.ncbi.nlm.nih.gov/nuccore/ET047429>.

(Continued)

*Primary Examiner* — Jason Deveau Rosen
(74) *Attorney, Agent, or Firm* — Arnold & Porter Kaye Scholer LLP

(57) ABSTRACT

Compositions and methods for modifying the production levels of alkaloids in plants are provided. Alkaloid production can be genetically controlled by modulating the transcriptional activation of PMT genes mediated by members of the ERF family and/or Myc family of transcription factors. Novel nucleotide sequences encoding the Myc family of transcription factors are also provided.

19 Claims, 16 Drawing Sheets

Specification includes a Sequence Listing.

(56) References Cited

OTHER PUBLICATIONS

GenBank Accession No. ET047460, "CHO_OF4615xb08r1.ab1 CHO_OF4 Nicotiana tabacum genomic 3', genomic survey sequence," Oct. 12, 2007. [retrieved on May 4, 2022] Retrieved from the internet: <URL:https://www.ncbi.nlm.nih.gov/nuccore/158194092>.
GenBank Accession No. ET048073. "CHO_OF4735xp20r1.ab1 CHO_OF4 Nicotiana tabacum genomic 3', genomic survey sequence," Oct. 12, 2007. [retrieved on May 4, 2022] Retrieved from the internet: <https://www.ncbi.nlm.nih.gov/nuccore/158194705?report=gss>.
Higgins et al., "CLUSTAL: a package for performing multiple sequence alignment on a microcomputer," *Gene*, 73(1): 237-244 (1988).
Higgins et al., "Fast and sensitive multiple sequence alignments on a microcomputer," *Bioinformatics*, 5(2): 151-153 (1989).
Huang et al., "Parallelization of a local similarity algorithm," *Bioinformatics*, 8(2):155-165 (1992).
International Search Report dated May 8, 2009, issued in International Patent Application No. PCT/US2008/010447, 4 pages.
Karlin et al., "Applications and statistics for multiple high-scoring segments in molecular sequences," *PNAS*, 90 (12) 5873-5877 (1993).
Kitajima et al., "Characterization of Gene Expression of NsERFs, Transcription Factors of Basic PR Genes from *Nicotiana sylvesteris," Plant Cell Physiol*. 41, pp. 817-824 (2000).
Ohme-Takagi et al., "Ethylene-inducible DNA binding proteins that interact with an ethylene-responsive element," *The Plant Cell*, 7(2): 173-182 (1995).
Pearson et al., "Using the FASTA Program to Search Protein and DNA Sequence Databases,", *Methods in Molecular Biology*, 24: 307-331 (1994) (abstract only).
Qu et al., "Artificial MicroRNA-Mediated Virus Resistance in Plants," *Journal of Virology*, 81(12):6690-6699 (2007).
Sato et al., "Metabolic engineering of plant alkaloid biosynthesis," *PNAS*, 98(1):367-372 (2001).
Todd et al., "A functional genomics screen identifies diverse transcription factors that regulate alkaloid biosynthesis in Nicotiana benthamiana," *The Plant Journal*, 62(4):589-600 (2010).
UniProt_submission Q700C0_SOL TU. Jul. 5, 2004. [retrieved on Apr. 23, 2009] Retrieved from the internet:<URL: http://www.genome.jp/dbget-bin/www_bget?iniprot+Q700CO_SOLTU>.
Wielopolska et al., "A high-throughput inducible RNAi vector for plants," *Plant Biotechnology Journal*, 3(6):583-590 (2005).
Xu et al., "Methyl jasmonate induced expression of the tobacco putrescine N-methyltransferase genes requires both G-box and GCC-motif elements," *Plant Molecular Biology*, 55:743-761 (2004).
Zhang et al., "Tobacco Transcription Factors NtMYC2a and NtMYC2b Form Nuclear Complexes with the NtJAZ1 Repressor and Regulate Multiple Jasmonate-Inducible Steps in Nicotine Biosynthesis," *Molecular Plant*, 5(1):73-84 (2012).
Zuo et al., "Over-expression GbERF2 transcription factor in tobacco enhances brown spots disease resistance by activating expression of downstream genes," *Gene*, 391(1-2):80-90 (2007).
http://www.biology.wustl.edu/gcg/blast.html (printed on Oct. 15, 2018).

* cited by examiner

Binding activity: ERF5 > ERF2 > ERF3 >>ERF14

NtERF5 and NtERF2 are MeJA responsive, but with different kinetics

NtERF3 is ethylene responsive

NtMYC3 cDNA Sequence:

ATGACTGATTACAGCTTACCCACCATGAATTTGTGGAATACTAGTGGTACTACCGATGACAACGTTTCTATGAT
GGAATCTTTTATGTCTTCTGATCTCACTTCATTTTGGGCTACTTCTAATTCTACTACTGCTGCTGTTACCTCTAA
TTCTAATCTTATTCCAGTTAATACCCTAACTGTTCTTCTTCCGTCTTCTTGTGCTTCTACTGTCACAGCTGTGG
CTGTCGATGCTTCAAAATCCATGTCTTTTTTCAACCAAGAAACTCTTCAGCAGCGTCTTCAAACCCTCATTGAT
GGTGCTCGTGAGACGTGGACCTATGCCATCTTTTGGCAGTCATCCGTCGTTGATTTATCGAGTCCGTTTGTG
TTGGGCTGGGGAGATGGTTACTACAAAGGTGAAGAAGATAAAGCCAATAGGAAATTAGCTGTTTCTTCTCCT
GCTTATATTGCTGAGCAAGAACACCGAAAAAAGGTTCTCCGGGAGCTGAATTCGTTGATCTCCGGCACGCAA
ACCGGCACTGATGATGCCGTCGATGAAGAAGTTACCGACACTGAATGGTTCTTCCTTATTTCCATGACCCAAT
CGTTTGTTAACGGAAGTGGGCTTCCGGGTCAGGCCTTATACAATTCCAGCCCTATTTGGGTCGCCGGAGCAG
AGAAATTGGCAGCTTCCCACTGCGAACGGGCTCGGCAGGCCCAGGGATTCGGGCTTCAGACGATGGTTTGT
ATTCCTTCAGCAAACGGCGTGGTTGAATTGGGCTCCACGGAGTTGATAATCCAGAGTTGTGATCTCATGAAC
AAGGTTAGAGTATTGTTTAACTTCAATAATGATTTGGGCTCTGGTTCGTGGGCTGTGCAGCCCGAGAGCGAT
CCGTCCGCTCTTTGGCTCACTGATCCATCGTCTGCAGCTGTAGAAGTCCAAGATTTAAATACAGTTAAGGCAA
ATTCAGTTCCATCAAGTAATAGTAGTAAGCAAGTTGTGTTTGATAATGAGAATAATGGTCACAGTTCTGATAAT
CAGCAACAGCAGCATTCTAAGCATGAAACACAAGGATTTTTCACAAGGGAGTTGAATTTTTCAGAATTTGGGT
TTGATGGAAGTAGTAATAATAGGAATGGGAATTCATCACTTTCTTGCAAGCCAGAGTCGGGGGAAATCTTGAA
TTTTGGTGATAGTACTAAGAAAAGTGCAAATGGGAACTTATTTTCGGGTCAGTCCCATTTTGGGGCAGGGGA
GGAGAATAAGAACAAGAAAAGGTCACCTGCTTCCAGAGGAAGCAATGAAGAAGGAATGCTTTCATTTGTTTC
GGGTACAATCTTGCCTGCAGCTTCTGGTGCGATGAAGTCAAGTGGAGGTGTAGGTGAAGACTCTGATCATTC
GGATCTTGAGGCCTCAGTGGTGAAAGAAGCTGAAAGTAGTAGAGTTGTAGAACCCGAAAAGAGGCCAAAGAA
GCGAGGAAGGAAGCCAGCAAATGGACGGGAGGAACCTTTGAATCACGTCGAAGCAGAGAGGCAAAGGAGA
GAGAAATTAAACCAAAGGTTCTACGCATTAAGAGCTGTTGTTCCGAATGTGTCCAAGATGGACAAGGCATCAC
TGCTTGGAGATGCAATTTCATATATTAATGAGCTGAAGTTGAAGCTTCAAAATACAGAAACAGATAGAGAAGA
ATTGAAGAGCCAAATAGAAGATTTAAAGAAAGAATTAGTTAGTAAAGACTCAAGGCGCCCTGGTCCTCCACCA
TCAAATCATGATCACAAGATGTCTAGCCATACTGGAAGCAAGATTGTAGACGTGGATATAGATGTTAAGATAA
TTGGATGGGATGCGATGATTCGTATACAATGTAATAAAAAGAATCATCCAGCTGCAAGGTTAATGGTAGCCCT
CAAGGAGTTAGATCTAGATGTGCACCATGCCAGTGTTTCAGTGGTGAACGATTTGATGATCCAACAAGCCACT
GTGAAAATGGGTAGCAGACTTTACACGGAAGAGCAACTTAGGATAGCATTGACATCCAGAGTTGCTGAAACA
CGCTAA

FIG. 11

NtMYC3 Protein:

MTDYSLPTMNLWNTSGTTDDNVSMMESFMSSDLTSFWATSNSTTAAVTSNSNLIPVNTLTVLLP
SSCASTVTAVAVDASKSMSFFNQETLQQRLQTLIDGARETWTYAIFWQSSVVDLSSPFVLGWGD
GYYKGEEDKANRKLAVSSPAYIAEQEHRKKVLRELNSLISGTQTGTDDAVDEEVTDTEWFFLISM
TQSFVNGSGLPGQALYNSSPIWVAGAEKLAASHCERARQAQGFGLQTMVCIPSANGVVELGST
ELIIQSCDLMNKVRVLFNFNNDLGSGSWAVQPESDPSALWLTDPSSAAVEVQDLNTVKANSVPS
SNSSKQVVFDNENNGHSSDNQQQQHSKHETQGFFTRELNFSEFGFDGSSNNRNGNSSLSCKP
ESGEILNFGDSTKKSANGNLFSGQSHFGAGEENKNKKRSPASRGSNEEGMLSFVSGTILPAASG
AMKSSGGVGEDSDHSDLEASVVKEAESSRVVEPEKRPKKRGRKPANGREEPLNHVEAERQRR
EKLNQRFYALRAVVPNVSKMDKASLLGDAISYINELKLKLQNTETDREELKSQIEDLKKELVSKDS
RRPGPPPSNHDHKMSSHTGSKIVDVDIDVKIIGWDAMIRIQCNKKNHPAARLMVALKELDLDVHH
ASVSVVNDLMIQQATVKMGSRLYTEEQLRIALTSRVAETR

FIG. 12

NtMYC4 cDNA Sequence:

ATGACTGATTACAGCTTACCCACCATGAATTTGTGGAATACTAGTGGTACTACCGATGACAACGTTACTATGA
TGGAAGCTTTTATGTCTTCTGATCTCACTTCATTTTGGGCTACTTCTAATTCTACTGCTGTTGCTGCTGTTACC
TCTAATTCTAATCATATTCCAGTTAATACCCCAACGGTTCTTCTTCCGTCTTCTTGTGCCTCTACTGTCACAGC
TGTGGCTGTCGATGCTTCAAAATCCATGTCTTTTTTCAACCAAGAAACCCTTCAACAGCGTCTTCAAACGCTCA
TTGATGGTGCTCGTGAGACGTGGACCTATGCCATCTTTTGGCAGTCATCCGCCGTTGATTTAACGAGTCCGT
TTGTGTTGGGCTGGGGAGATGGTTACTACAAAGGTGAAGAAGATAAAGCCAATAGGAAATTAGCTGTTTCTTC
TCCTGCTTATATAGCTGAGCAAGAACACCGGAAAAAGGTTCTCCGGGAGCTGAATTCGTTGATTTCCGGCAC
GCAAACCGGCACTGATGATGCCGTCGATGAAGAAGTTACCGACACTGAATGGTTCTTCCTTATTTCCATGACC
CAGTCGTTTGTTAACGGAAGTGGGCTTCCGGGTCAGGCCTTATACAATTCCAGCCCTATTTGGGTCGCCGGA
GCAGAGAAATTGGCAGCTTCCCACTGCGAACGGGCTCGGCAGGCCCAGGGATTCGGGCTTCAGACGATGG
TTTGTATTCCTTCAGCAAACGGCGTGGTTGAATTGGGCTCCACGGAGTTGATTATTCAGAGTTCTGATCTCAT
GAACAAGGTTAGAGTATTGTTTAACTTCAATAATGATTTGGGCTCTGGTTCGTGGGCTGTGCAACCCGAGAG
CGATCCGTCCGCTCTTTGGCTCACTGATCCATCGTCTGCAGCTGTACAAGTCAAAGATTTAAATACAGTTGAG
GCAAATTCAGTTCCATCAAGTAATAGTAGTAAGCAAGTTGTATTTGATAATGAGAATAATGGTCACAGTTGTGA
TAATCAGCAACAGCACCATTCTCGGCAACAAACACAAGGATTTTTTACAAGGGAGTTGAACTTTTCAGAATTC
GGGTTTGATGGAAGTAGTAATAATAGGAATGGGAATTCATCACTTTCTTGCAAGCCAGAGTCGGGGGAAATC
TTGAATTTTGGTGATAGCACTAAGAAAAGTGCAAATGGGAACTTATTTTCCGGTCAGTCTCATTTTGGTGCAG
GGGAGGAGAATAAGAAGAAGAAAAGGTCACCTGCTTCCAGAGGAAGCAATGAAGAAGGAATGCTTTCATTTG
TTTCAGGTACAATCTTGCCTGCAGCTTCTGGTGCGATGAAGTCAAGTGGATGTGTCGGTGAAGACTCCTCTG
ATCATTCGGATCTTGAGGCCTCAGTGGTGAAAGAAGCTGAAAGTAGTAGAGTTGTAGAACCCGAAAAGAGGC
CAAAGAAGCGAGGAAGGAAGCCAGCAAATGGACGTGAGGAACCTTTGAATCACGTCGAAGCAGAGAGGCAA
AGGAGAGAGAAATTAAACCAAAGGTTCTACGCTTTAAGAGCTGTTGTTCCGAATGTGTCCAAGATGGACAAG
GCATCACTGCTTGGAGATGCAATTTCATATATTAATGAGCTGAAGTTGAAGCTTCAAACTACAGAAACAGATA
GAGAAGACTTGAAGAGCCAAATAGAAGATTTGAAGAAAGAATTAGATAGTAAAGACTCAAGGCGCCCTGGTC
CTCCACCACCAAATCAAGATCACAAGATGTCTAGCCATACTGGAAGCAAGATTGTAGATGTGGATATAGATGT
TAAGATAATTGGATGGGATGCGATGATTCGTATACAATGTAATAAAAAGAACCATCCAGCTGCAAGGTTAATG
GTAGCCCTCAAGGAGTTAGATCTAGATGTGCACCATGCCAGTGTTTCAGTGGTGAATGATTTGATGATCCAAC
AAGCCACAGTGAAAATGGGTAGCAGACTTTACACGGAAGAGCAACTTAGGATAGCATTGACATCCAGAGTTG
CTGAAACACGCTAA

FIG. 13

NtMYC4 Protein:

MTDYSLPTMNLWNTSGTTDDNVTMMEAFMSSDLTSFWATSNSTAVAAVTSNSNHIPVNTPTVLL
PSSCASTVTAVAVDASKSMSFFNQETLQQRLQTLIDGARETWTYAIFWQSSAVDLTSPFVLGWG
DGYYKGEEDKANRKLAVSSPAYIAEQEHRKKVLRELNSLISGTQTGTDDAVDEEVTDTEWFFLIS
MTQSFVNGSGLPGQALYNSSPIWVAGAEKLAASHCERARQAQGFGLQTMVCIPSANGVVELGS
TELIIQSSDLMNKVRVLFNFNNDLGSGSWAVQPESDPSALWLTDPSSAAVQVKDLNTVEANSVP
SSNSSKQVVFDNENNGHSCDNQQQHHSRQQTQGFFTRELNFSEFGFDGSSNNRNGNSSLSCK
PESGEILNFGDSTKKSANGNLFSGQSHFGAGEENKKKKRSPASRGSNEEGMLSFVSGTILPAAS
GAMKSSGCVGEDSSDHSDLEASVVKEAESSRVVEPEKRPKKRGRKPANGREEPLNHVEAERQ
RREKLNQRFYALRAVVPNVSKMDKASLLGDAISYINELKLKLQTTETDREDLKSQIEDLKKELDSK
DSRRPGPPPPNQDHKMSSHTGSKIVDVDIDVKIIGWDAMIRIQCNKKNHPAARLMVALKELDLDV
HHASVSVVNDLMIQQATVKMGSRLYTEEQLRIALTSRVAETR

FIG. 14

NtERF2 cDNA Sequence:

ATGTATCAACCAATTTCGACCGAGCTACCTCCGACGAGTTTCAGTAGT
CTCATGCCATGTTTGACGGATACATGGGGTGACTTGCCGTTAAAAGTT
GATGATTCCGAAGATATGGTAATTTATGGGCTCTTAAGTGACGCTTTAA
CTGCCGGATGGACGCCGTTTAATTTAACGTCCACCGAAATAAAAGCCG
AGCCGAGGGAGGAGATTGAGCCAGCTACGATTCCTGTTCCTTCAGTG
GCTCCACCTGCGGAGACTACGACGGCTCAAGCCGTTGTTCCCAAGGG
GAGGCATTATAGGGGCGTTAGGCAAAGGCCGTGGGGGAAATTTGCGG
CGGAAATAAGGGACCCAGCTAAAAACGGCGCACGGGTTTGGCTAGGG
ACTTATGAGACGGCTGAAGAAGCCGCGCTCGCTTATGATAAAGCAGCT
TACAGGATGCGCGGCTCCAAGGCTCTATTGAATTTTCCGCATAGGATC
GGCTTAAATGAGCCTGAACCGGTTAGACTAACCGCTAAGAGACGATCA
CCTGAACCGGCTAGCTCGTCAATATCATCGGCTTTGGAAAATGGCTCG
CCGAAACGGAGGAGAAAAGCTGTAGCGGCTAAGAAGGCTGAATTAGA
AGTGCAAAGCCGATCAAATGCTATGCAAGTTGGGTGCCAGATGGAACA
ATTTCCAGTTGGCGAGCAGCTATTAGTCAGTTAA

FIG. 15

NtERF5 cDNA Sequence:

ATGTCAAGTAACTCAAGCCCACTAGAAATAGACACTTCATTTTCACATT
CCAACTTCTTCTTTCTCCAAGATCAATCACCAATTTTACAATGGGATGAT
GATCTTTTCTTCAATGATCCATGGTTTGATGATGATCAATCACCAATTAT
ACCATGTAACTCAGAGAAAGATGAAAATCATCAAGTATTTGAAGAATCC
TCAGACAATACAATCATGTCAAAAGGAAGTAGCCATGGTCAAGAATTAG
AAGAGGTAACATCCCAAGAAGAAAAAGAAAAAGAAGAAGAAGAAAAAC
ACTATATAGGAGTTAGAAAAAGGCCATGGGGTAAATATGCAGCAGAAA
TAAGAGATTCAACAAGAAATGGAATTAGGGTTTGGTTAGGGACATTTGA
TACAGCTGAAGAAGCTGCTTTAGCTTATGATCAAGCTGCATTATCGATG
AGAGGTCCTTGGTCTCTTCTTAATTTTCCATTGGAGAAAGTCAAGAAAT
CACTTGAAAAAATTGAGTATTCTTGTAAAGATGGATTGTCTCCTGCTGC
TGTTCTAAAAGCTACTCATAAAACAAGGAGAGTGAAGCATAAAAGAAGT
AGTAGAAAGAAAAAGAATAAAGAAACTCATAATGTTATTGTTTTTGAGG
ACTTGGGTGCTGAGTTATTAGAAGAGCTTTTAATGACTTCATCACAACA
TTCGTGTCGAAGGGACTGA

FIG. 16

COMPOSITIONS AND RELATED METHODS FOR MODULATING ALKALOID PRODUCTION BY CONTROLLING PMT PROMOTER ACTIVATION MEDIATED BY TRANSCRIPTIONAL FACTORS ERF AND Myc

CROSS-REFERENCE TO RELATED APPLICATIONS

This application is a continuation of U.S. application Ser. No. 18/363,120, filed on Aug. 1, 2023 (now U.S. Pat. No. 12,054,523), which is a continuation of U.S. Application Ser. No. 17/517,305, filed Nov. 2, 2021, (now U.S. Pat. No. 11,760,781), which is a continuation of U.S. application Ser. No. 16/369,614, filed Mar. 29, 2019, (now U.S. Pat. No. 11,681,118), which is a continuation of U.S. application Ser. No. 15/644,199, filed Jul. 7, 2017 (now U.S. Pat. No. 10,280,203), which is a divisional of U.S. application Ser. No. 14/311,684, filed Jun. 23, 2014 (which is now U.S. Pat. No. 9,701,978), which is a continuation of U.S. application Ser. No. 12/676,871, filed Nov. 10, 2010 (which is now U.S. Pat. No. 8,759,101), which is a U.S. National Stage entry of International Application No. PCT/US2008/010447, filed Sep. 5, 2008, which claims the benefit of both U.S. Provisional Application No. 60/935,948, filed Sep. 7, 2007, and U.S. Provisional Application No. 60/935,947, filed Sep. 7, 2007, all of which are incorporated by reference herein in their entireties.

INCORPORATION OF SEQUENCE LISTING

A sequence listing encoded as XML in UTF-8 text and contained in the file named "P34679US16_SQ" which is 19,045 bytes (measured in MS-Windows®) and created on Jul. 26, 2023, is filed electronically herewith and incorporated by reference in its entirety.

BACKGROUND

Nicotine production from polyamine putrescine, a precursor of nicotine, can be produced by two pathways in plants. Putrescine can be synthesized directly from ornithine in a reaction catalyzed by the enzyme ornithine decarboxylase, or can be produced indirectly from arginine in a sequence of reactions initiated by arginine decarboxylase. The first committed step in nicotine biosynthesis is the conversion of putrescine to N-methylputrescine by putrescine N-methyltransferase ("PMT"). N-methylputrescine is subsequently oxidized by a diamine oxidase, and is cyclized to produce a 1-methyl-$\Delta^1$-pyrrolium cation, which is subsequently condensed with nicotinic acid to produce nicotine.

There is a need for compositions and improved methods for genetically regulating the production levels of nicotine and other alkaloids in plants, including transgenic plants, transgenic tobacco plants, recombinant stable cell lines, recombinant stable tobacco cell lines, and derivatives thereof.

SUMMARY

In various embodiments, compositions and methods for modifying the production levels of nicotine and other alkaloids in plants are provided. Nicotine and other alkaloid production can be genetically modified by modulating the transcriptional activation of PMT genes mediated by members of the ERF family and/or Myc family of transcriptional factors.

BRIEF DESCRIPTION OF DRAWINGS

FIG. 11 shows the polynucleotide sequence for NtMyc3 cDNA (SEQ ID NO:1).

FIG. 12 shows the polypeptide sequence for NtMyc3 protein (SEQ ID NO:2).

FIG. 13 shows the polynucleotide sequence for NtMyc4 cDNA (SEQ ID NO:3).

FIG. 14 shows the polypeptide sequence for NtMyc4 protein (SEQ ID NO:4).

FIG. 15 shows the polynucleotide sequence for NtERF2 cDNA (SEQ ID NO:5).

FIG. 16 shows the polynucleotide sequence for NtERF5 cDNA (SEQ ID NO:6).

DETAILED DESCRIPTION

Regulation of nicotine biosynthesis is desirable in a variety of plants, especially in tobacco plants. Nicotine biosynthesis can be regulated by controlling the expression levels and/or the activities of enzymes involved in the nicotine biosynthetic pathway. In particular, an effective way to genetically regulate nicotine production is by controlling the transcriptional activation of promoters that control the expression of genes encoding putrescine N-methyltransferases ("PMT"). PMT is one of several critical enzymes involved in the nicotine biosynthetic pathway in plants, including tobacco plants. Various compositions and methods for modifying PMT expression levels in plants are provided, as further described below.

The production levels of nicotine, other alkaloids, and secondary metabolites can be genetically regulated by controlling the expression level of PMT, which correlates directly with their production levels. This can be accomplished by controlling PMT promoter activation that correlates with the expression levels of the PMT structural gene. PMT RNA transcripts produced by transcriptional processes are subsequently translated into PMT polypeptides that exhibit PMT enzymatic activity. The activation of the PMT promoter by sequence-specific transcriptional factors ("transcriptional activators") can increase the levels of PMT RNA transcripts and PMT polypeptides produced. In contrast, the repression of the PMT promoter by sequence-specific transcriptional factors ("transcriptional repressors") can decrease the levels of PMT RNA transcripts and PMT polypeptides produced.

Figure 1:
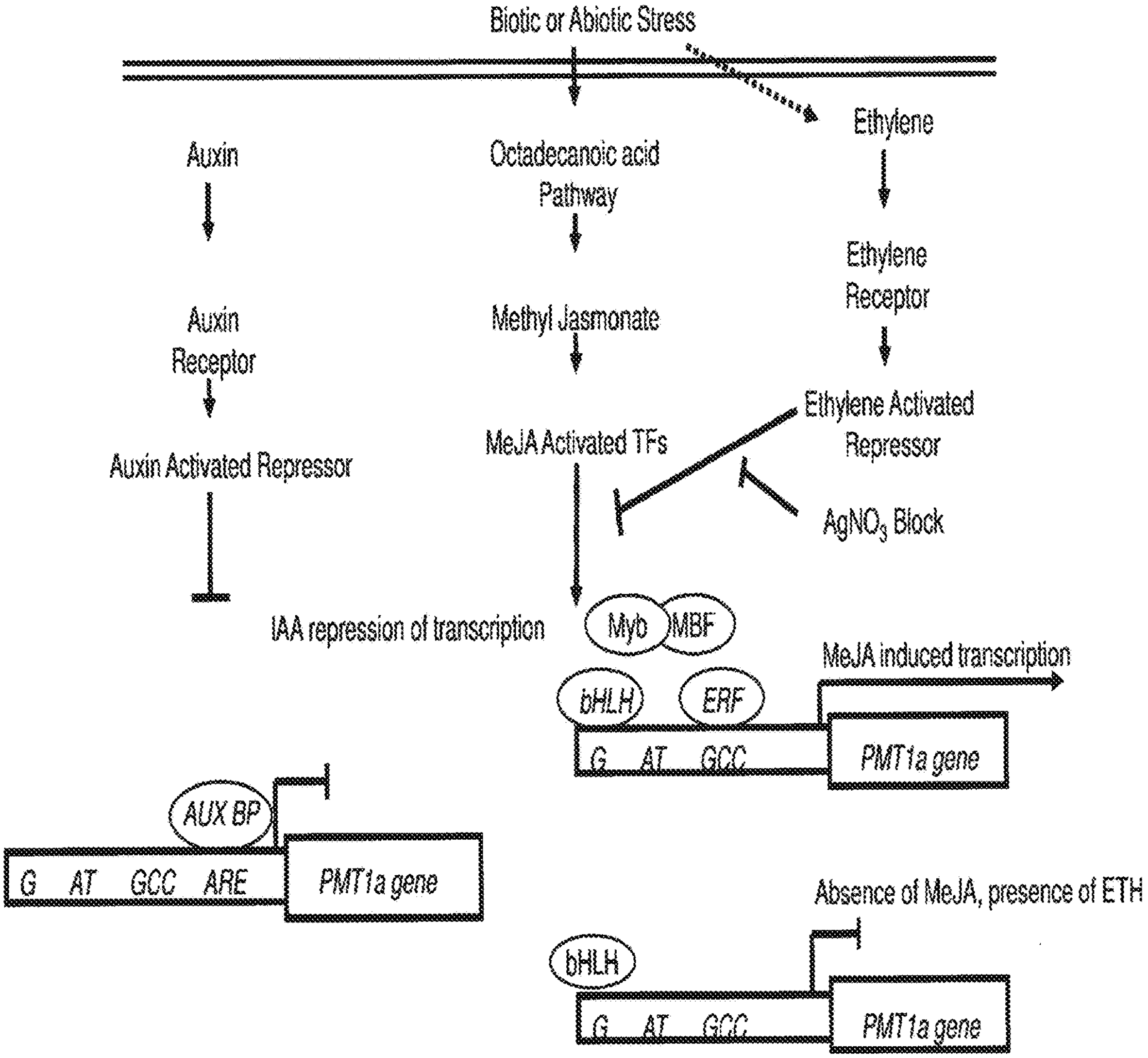
FIG. 1 illustrates multiple signal transduction pathways, induced by various stimuli that regulate PMT promoter activation/repression in plants.
Figures 2A, 2B, 2C:
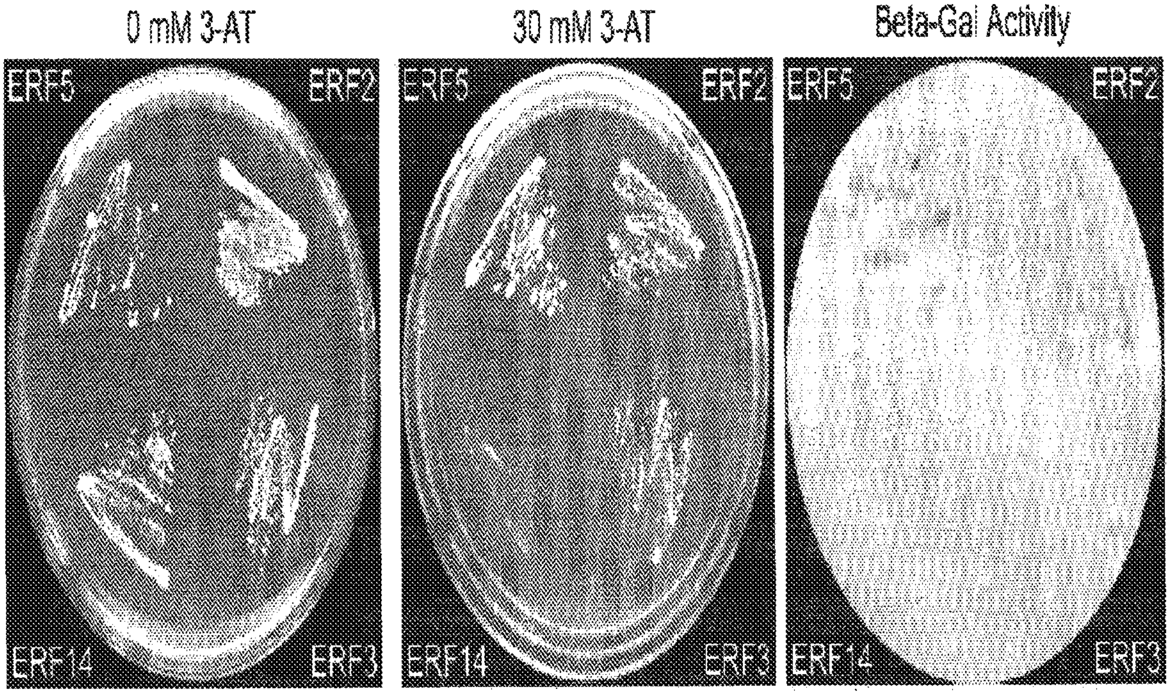
FIGS. 2A-2C show the identification of transcription factors of the ERF family that can bind specifically to the GAG motif.
Figures 3A, 3B, 3C:
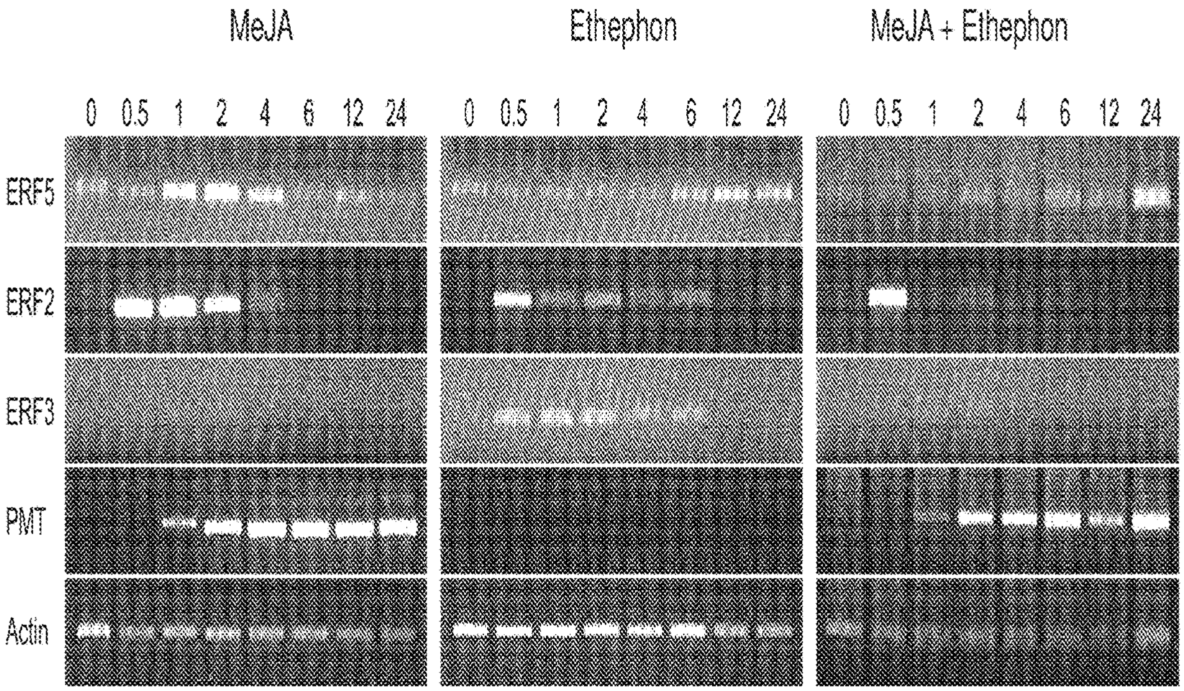
FIGS. 3A-3C show relative expression levels of transcripts for NtERF2, NtERF3, and NtERF5, measured by RT-PCR in BY-2 cell extracts. The expression levels of NtERF2 and NtERF5 were responsive to MeJA-inducible pathway. The expression level of NtERF3 was responsive to ethylene (or ethephon) inducible pathway.
Figure 4:
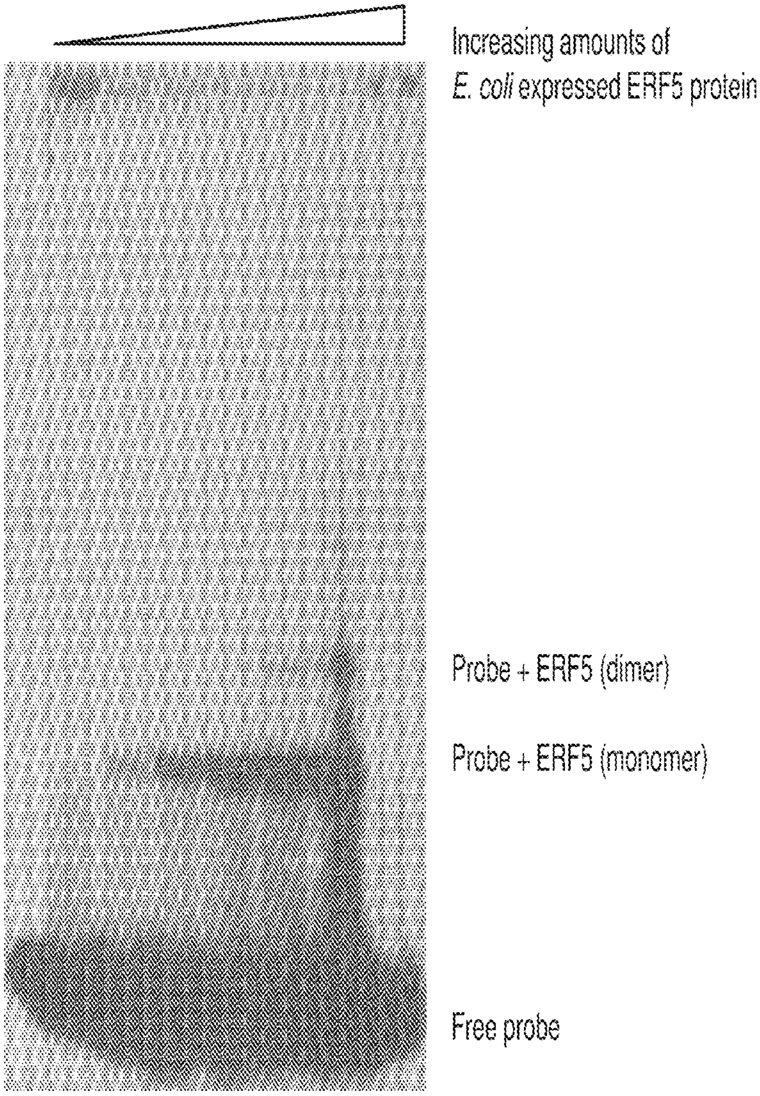
FIG. 4 shows that NtERF5 can bind to the GAG motif by in vitro gel mobility shift assay.
Figure 5A:
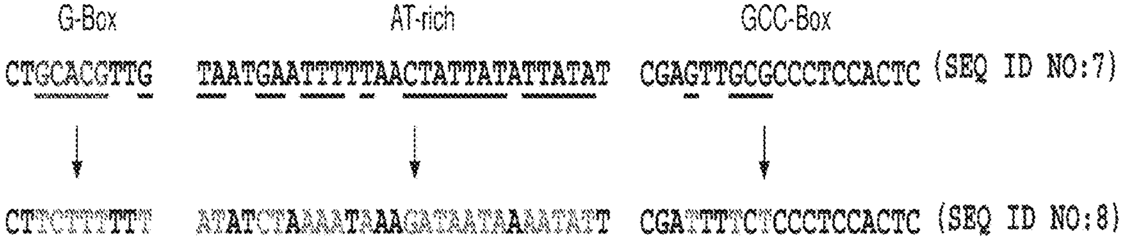
FIGS. 5A-5C show that NtERF5 can activate the NtPMT1a promoter by binding to the AT-rich region of the GAG motif.
Figure 5B:
Figure 5C:
Figure 5C:
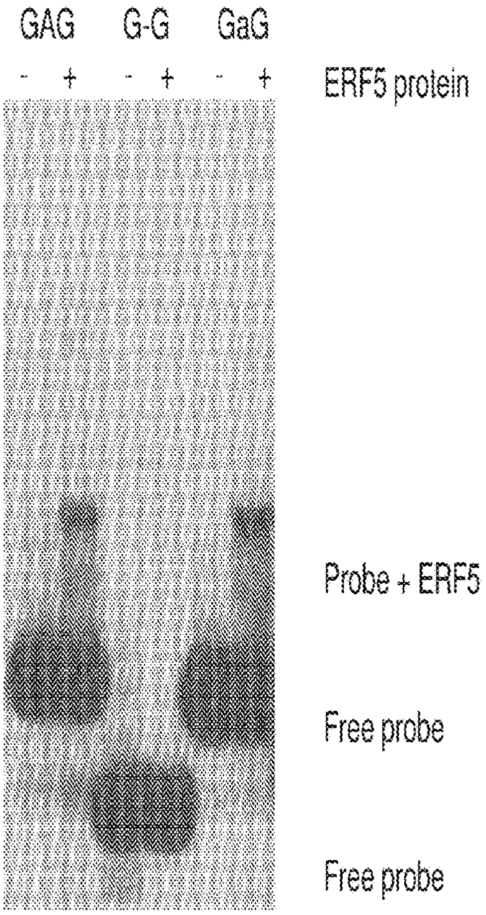
Figure 6A:
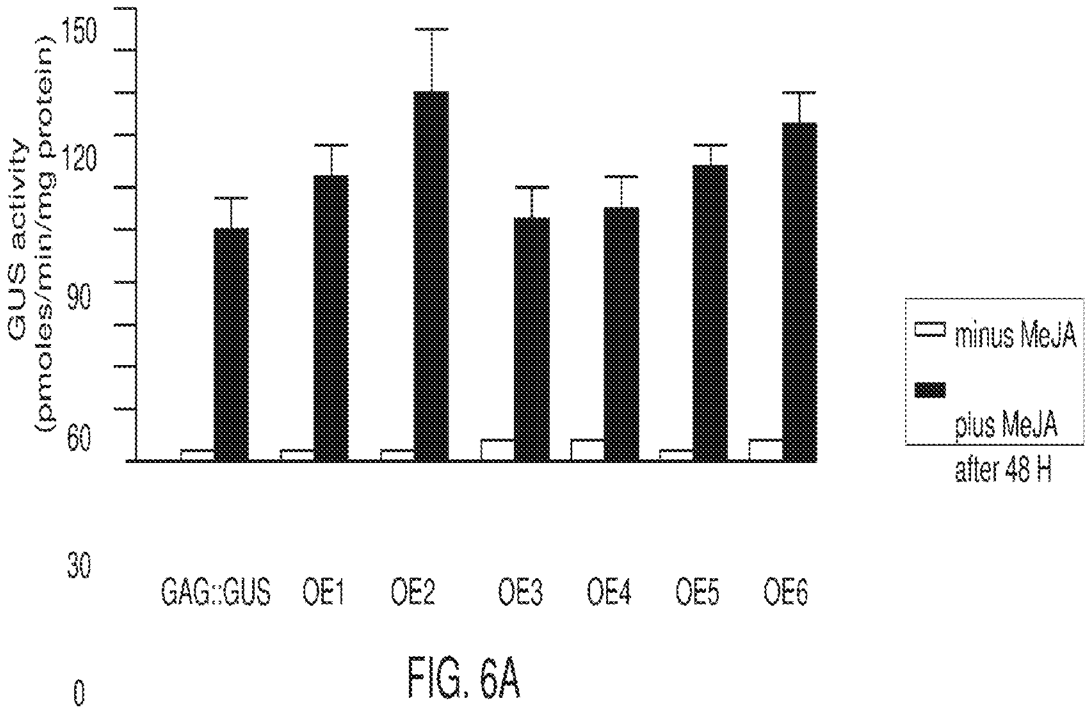
FIG. 6A shows that NtERF5 over-expression results in GUS reporter expression in a MeJA-dependent manner by binding to 4xGAG motifs positioned upstream of a promoter that drives GUS reporter expression. Overexpressed cell lines ("OE") that have been stably integrated with 4XGAG::GUS reporter were transiently transfected with expression vectors over-expressing NtERF5.
Figure 6B:
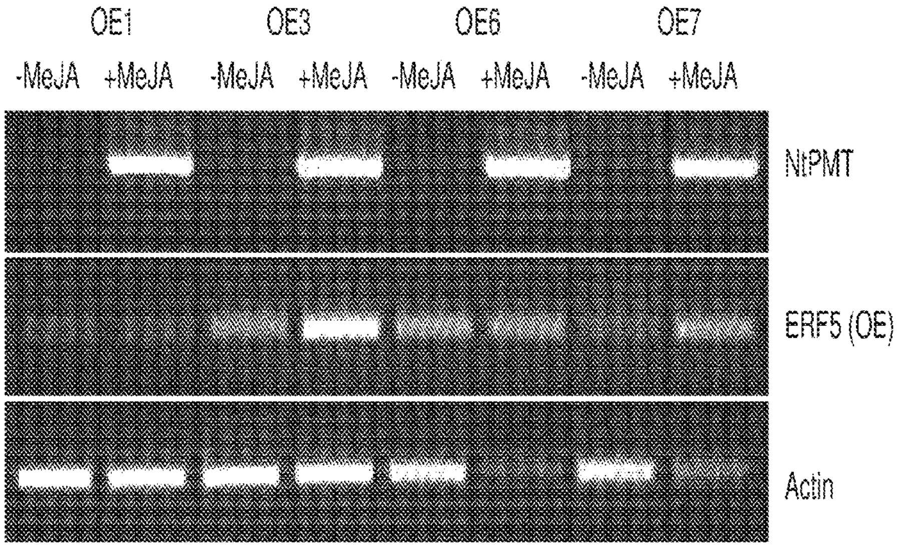
FIG. 6B shows that NtERF5 over-expression is not sufficient to activate NtPMT expression in the absence of MeJA. NtPMT transcripts were detected in extracts of cell lines that were induced by MeJA.
Figure 7:
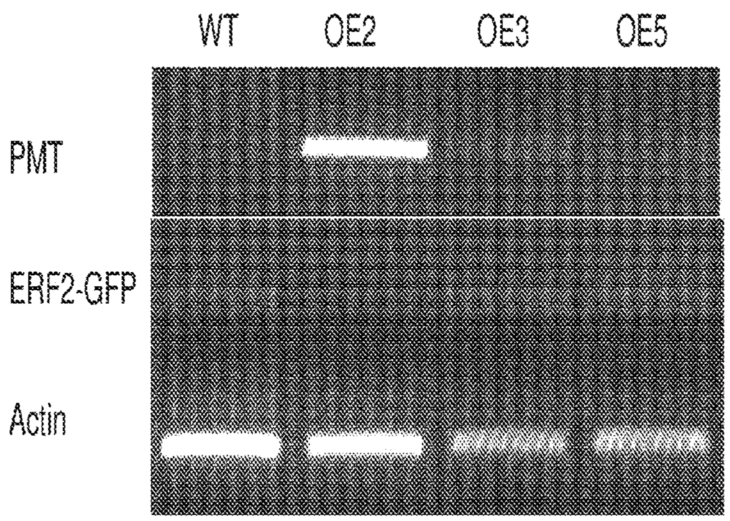
FIG. 7 shows that NtERF2 over-expression activates NtPMT expression in a MeJA-independent manner.
Figures 8A, 8B, 8C:
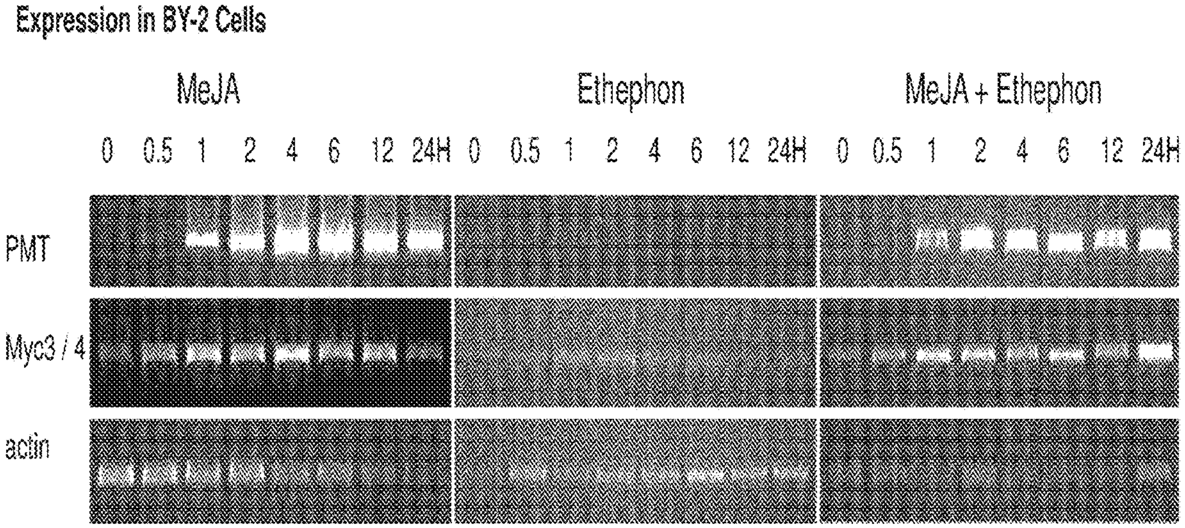
FIGS. 8A-8C show that Myc3/Myc4 over-expression in BY-2 cells is inducible by MeJA.
Figure 8D:
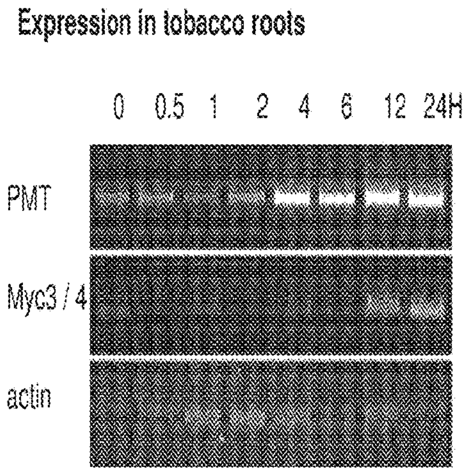
FIG. 8D shows that Myc3/Myc4 over-expression in the roots of transgenic tobacco is inducible by MeJA.
Figure 9:
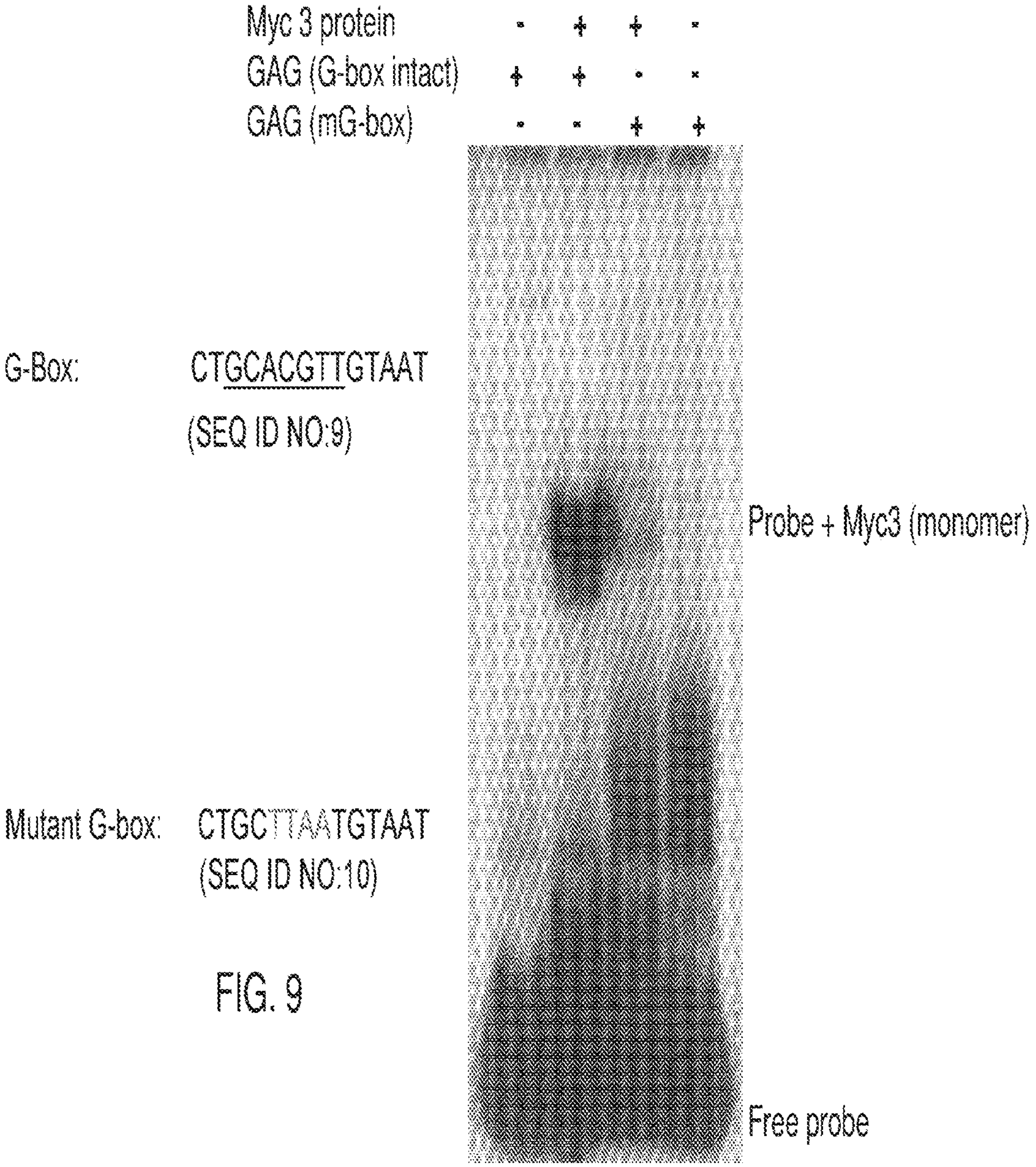
FIG. 9 shows that Myc3 binds the G-box of the GAG motif by in vitro mobility shift assay.
Figure 10:
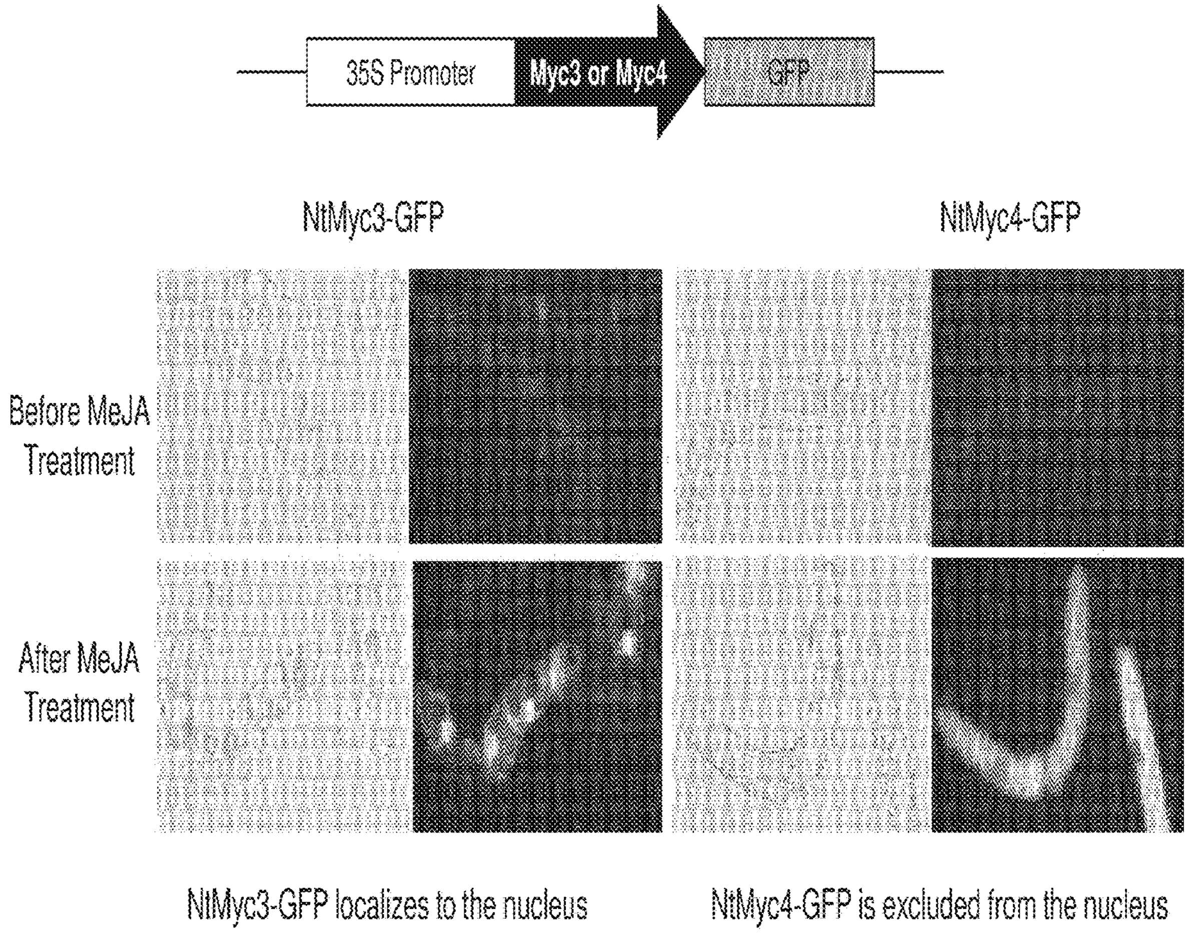
FIG. 10 shows differential localization of Myc3 and Myc4, respectively, in BY-2 cells after MeJA exposure. NtMyc3-GFP localized to the nucleus after MeJA exposure. In contrast, NtMyc4-GFP was excluded from the nucleus after MeJA exposure.

PMT promoter activation is responsive to various endogenous and exogenous signals, including phytohormones, wounding, and invasion by pathogens or insects. FIG. 1 illustrates the existence of multiple signal transduction pathways inducible by various phytohormones, including jasmonic acid ("JA"), auxin, and ethylene, which can affect PMT promoter activation. As shown in FIG. 1, the transcriptional regulation of PMT genes can be responsive to multiple signal transduction pathways that can be co-induced if multiple stimulants exist simultaneously in an environment. When a particular signal transduction pathway is induced, the expression level and/or the transcriptional activity of a transcriptional factor can be increased. Alternatively, the expression level and/or the transcriptional activity of a transcriptional factor can be decreased by inducing a particular signal transduction pathway. For example, a JA-inducible signal transduction pathway can be blocked by co-exposure to sufficient concentrations of auxin and/or ethylene that appear to have antagonistic effects on the JA-inducible pathway. In particular, PMT promoter activation induced by JA exposure can be blocked by exposure to auxin and/or ethylene.

In various plants, such as tobacco, the phytohormone jasmonic acid ("JA") (3-oxo-2-(cis-2-pentenyl)-1-cyclopentaneacetic acid) and/or its methylated ester derivative ("MeJA") can be utilized for inducing nicotine production. JA and/or MeJA can be utilized for inducing the expression of genes involved in the biosynthesis of secondary metabolites such as alkaloids, flavonoids, and terpenoids. Furthermore, JA and/or MeJA can be utilized to control various processes that regulate plant growth and environmental adaptation, including seed germination, regulation of carbon and nitrogen storage, photosynthesis, senescence, pollen development, fruit ripening, wound responses, and resistance to insects and pathogens. For regulating defense responses, JA and/or MeJA can be utilized to act synergistically with, or antagonistically against, two other plant hormones, salicylic acid (SA) and ethylene. JA and/or MeJA can be utilized for inducing the expression of genes encoding proteinase inhibitors involved in pest resistance and genes encoding defensins that exhibit antimicrobial activity. Therefore, various wound-induced and stress-induced biological responses of interest can be elicited by controlling the amount and extent of exposure to such phytohormones.

In *Nicotiana tabacum*, at least five PMT genes have been characterized: NtPMT1a, NtPMT1b, NtPMT2, NtPMT3, and NtPMT4. PMT gene expression in the roots of *N. tabacum* can be up-regulated by various stimuli, including topping procedures, the physical invasion by insects and/or other herbivores, and JA or MeJA exposure.

This disclosure describes a regulatory region upstream of the core promoter elements of PMT promoters, referred to as the "GAG motif," that confers PMT promoters with responsiveness to JA and MeJA. The GAG motif comprises a G-box like element, an AT-rich element, and a GCC-like box element. The GAG motif functions optimally as an intact, tripartite unit, in that the three elements must be utilized together, and must be arranged so that the G-box like element is positioned upstream of the AT-rich element, which is positioned upstream of the GCC-like box element.

Based on experimental studies described herein, the GAG and the G-G derivative fragment (similar to the structure of the GAG motif but deficient in the AT-rich element) have been shown to be responsive to JA and MeJA when plants are exposed to these phytohormones. The JA and MeJA responsiveness of the GAG motif can be mediated by members of the ERF and Myc families of transcriptional factors, as described herein. The GAG motif confers the recruitment of ERF and Myc transcriptional factors and other transcriptional factors when operably-linked to a promoter of interest, which is operably-linked to a transgene of interest positioned downstream of the promoter of interest. Suitable transgenes include genes that encode various enzymes involved in the biosynthesis of alkaloids, nicotine, and flavonoids, for example.

The sub-elements of the GAG motif that can recruit particular members of the ERF and Myc families have been further characterized by results described herein. For example, the experimental results show that ERF2/ERF3/ERF5 are recruited to the GAG motif in a JA-inducible manner. This occurs through the GCC-like box element and requires some or all of the AT-rich element for recruitment. For example, the experimental results show that the G-box element can recruit NtMyc3/NtMyc4 in a JA-inducible manner.

For up-regulating or down-regulating various promoters of interest, the following compositions and methods are contemplated:

In general, various embodiments are directed to expression vectors that enable the over-expression of transcriptional factors, NtMyc3, NtMyc4, NtERF2, and/or NtERF5, for modulating the production levels of nicotine, other alkaloids, including various flavonoids. These expression vectors can be transiently introduced into host plant cells or stably integrated into the genomes of host plant cells to generate transgenic plants by various methods known to persons skilled in the art. When these expression vectors are stably integrated into the genomes of host plant cells to generate stable cell lines or transgenic plants, the over-expression of transcriptional factors, NtMyc3, NtMyc4, NtERF2, and/or NtERF5, can be utilized as a method for modulating the promoter activation of endogenous promoters that are responsive to these transcriptional factors. Furthermore, such host plant cells can be further manipulated to receive heterologous promoter constructs that are responsive to transcriptional factors, NtMyc3, NtMyc4, NtERF2, and/or NtERF5. Furthermore, such host plant cells can be further manipulated to receive heterologous promoter constructs that have been modified by incorporating one or more GAG motifs upstream of the core elements of the heterologous promoter of interest.

Any promoter of interest can be manipulated to be responsive to JA and MeJA by incorporating one or more GAG motifs and/or derivative GAG motifs upstream of the promoter of interest. Suitable promoters include various promoters of any origin that can be activated by the transcriptional machinery of plant cells, such as various homologous or heterologous plant promoters and various promoters derived from plant pathogens, including bacteria and viruses. Suitable promoters include constitutively active promoters and inducible promoters.

For various expression vectors described below, various genes that encode enzymes involved in biosynthetic pathways for the production of alkaloids, flavonoids, and nicotine can be suitable as transgenes that can be operably-linked to a promoter of interest.

In another embodiment, an expression vector comprises a promoter operably-linked to the cDNA encoding Myc3, Myc4, ERF2, and/or ERF5. In another embodiment, a plant cell line comprises an expression vector comprising a promoter operably-linked to the cDNA encoding Myc3, Myc4, ERF2, and/or ERF5. In another embodiment, a transgenic plant comprises an expression vector comprising a promoter operably-linked to the cDNA encoding Myc3, Myc4, ERF2, and/or ERF5. In another embodiment, methods for genetically modulating the production of alkaloids, flavonoids, and nicotine are provided, comprising: introducing an expression vector comprising a promoter operably-linked to the cDNA encoding Myc3, Myc4, ERF2, and/or ERF5.

In another embodiment, an expression vector comprises a first promoter operably-linked to cDNA encoding Myc3, Myc4, ERF2, and/or ERF5; and a second promoter operably-linked to cDNA encoding an enzyme involved in the biosynthesis of alkaloids. In another embodiment, a plant cell line comprises an expression vector comprising a first promoter operably-linked to cDNA encoding Myc3, Myc4, ERF2, and/or ERF5; and a second promoter operably-linked to cDNA encoding an enzyme involved in the biosynthesis of alkaloids. In another embodiment, a transgenic plant comprises an expression vector comprising a first promoter operably-linked to cDNA encoding Myc3, Myc4, ERF2, and/or ERF5; and a second promoter operably-linked to cDNA encoding an enzyme involved in the biosynthesis of alkaloids. In another embodiment, methods for genetically modulating the production level of alkaloids are provided, comprising: introducing an expression vector comprising a first promoter operably-linked to cDNA encoding Myc3, Myc4, ERF2, and/or ERF5; and a second promoter operably-linked to cDNA encoding an enzyme involved in the biosynthesis of alkaloids.

In another embodiment, an expression vector comprises a first promoter operably-linked to cDNA encoding Myc3, Myc4, ERF2, and/or ERF5; and a second promoter operably-linked to cDNA encoding an enzyme involved in the biosynthesis of flavonoids. In another embodiment, a plant cell line comprises an expression vector comprising a first promoter operably-linked to cDNA encoding Myc3, Myc4, ERF2, and/or ERF5; and a second promoter operably-linked to cDNA encoding an enzyme involved in the biosynthesis of flavonoids. In another embodiment, a transgenic plant comprises an expression vector comprising a first promoter operably-linked to cDNA encoding Myc3, Myc4, ERF2, and/or ERF5; and a second promoter operably-linked to cDNA encoding an enzyme involved in the biosynthesis of flavonoids. In another embodiment, methods for modulating the production level of flavonoids are provided, comprising: introducing an expression vector comprising a first promoter operably-linked to cDNA encoding Myc3, Myc4, ERF2, and/or ERF5; and a second promoter operably-linked to cDNA encoding an enzyme involved in the biosynthesis of flavonoids.

In another embodiment, an expression vector comprises a first promoter operably-linked to cDNA encoding Myc3, Myc4, ERF2, and/or ERF5; and a second promoter operably-linked to cDNA encoding an enzyme involved in nicotine biosynthesis. In another embodiment, a plant cell line comprises an expression vector comprising a first promoter operably-linked to cDNA encoding Myc3, Myc4, ERF2, and/or ERF5; and a second promoter operably-linked to cDNA encoding an enzyme involved in nicotine biosynthesis. In another embodiment, a transgenic plant comprises an expression vector comprising a first promoter operably-linked to cDNA encoding Myc3, Myc4, ERF2, and/or ERF5; and a second promoter operably-linked to cDNA encoding an enzyme involved in nicotine biosynthesis. In a preferred embodiment, the enzyme is PMT involved in nicotine biosynthesis. In another embodiment, methods for genetically modulating the production level of nicotine are provided, comprising: introducing an expression vector comprising a first promoter operably-linked to cDNA encoding Myc3, Myc4, ERF2, and/or ERF5; and a second promoter operably-linked to cDNA encoding an enzyme involved in nicotine biosynthesis. FIG. 11 shows the polynucleotide sequence for NtMyc3 cDNA (SEQ ID NO:1). FIG. 12 shows the polypeptide sequence for NtMyc3 protein (SEQ ID NO:2). FIG. 13 shows the polynucleotide sequence for NtMyc4 cDNA (SEQ ID NO:3). FIG. 14 shows the polypeptide sequence for NtMyc4 protein (SEQ ID NO:4). FIG. 15 shows the polynucleotide sequence for NtERF2 cDNA (SEQ ID NO:5), which encodes for Ethylene-responsive transcription factor 2 (Swiss Protein Accession No. Q40479; Plant Cell 7 (2), p 173-182 (1995; PUBMED #7756828). FIG. 16 shows the polynucleotide sequence for NtERF5 cDNA (SEQ ID NO:6), which encodes ERF Transcription Factor 5 (NCBI Accession No. AY655738; Mol. Plant Microbe Interact. 17 (10), p 1162-1171 (2004); PUBMED #15497409). NtERF5 cDNA (SEQ ID NO:6) also refers to sequence published in Mol. Plant Microbe Interact. 17 (10), p 1162-1171 (2004).

Another embodiment is directed to an isolated cDNA encoding NtMyc3 (SEQ ID NO:1), or fragments thereof. Another embodiment is directed to an isolated cDNA encoding NtMyc3 and having at least 85%, 90%, 95%, 96%, 97%, 98%, and 99% sequence identity to SEQ ID NO:1, or variant fragments thereof.

Another embodiment is directed to an isolated cDNA encoding NtMyc4 (SEQ ID NO:3), or fragments thereof. Another embodiment is directed to an isolated cDNA encoding NtMyc4 and having at least 85%, 90%, 95%, 96%, 97%, 98%, and 99% sequence identity to SEQ ID NO:3, or variant fragments thereof.

Another embodiment is directed to an isolated polypeptide NtMyc3 (SEQ ID NO:2), or fragments thereof. Another embodiment is directed to an isolated polypeptide NtMyc3 and having at least 85%, 90%, 95%, 96%, 97%, 98%, and 99% sequence identity to SEQ ID NO:2, or fragments thereof.

Another embodiment is directed to an isolated polypeptide NtMyc4 (SEQ ID NO:4), or fragments thereof. Another embodiment is directed to an isolated polypeptide NtMyc4 and having at least 85%, 90%, 95%, 96%, 97%, 98%, and 99% sequence identity to SEQ ID NO:4, or variant fragments thereof.

Another embodiment is directed to an expression vector comprising an isolated cDNA encoding NtMyc3 (SEQ ID NO:1), or fragments thereof. Another embodiment is directed to an expression vector comprising an isolated cDNA encoding NtMyc3 and having at least 85%, 90%, 95%, 96%, 97%, 98%, and 99% sequence identity to SEQ ID NO:1, or fragments thereof.

Another embodiment is directed to an expression vector comprising an isolated cDNA encoding NtMyc4 (SEQ ID NO:3), or fragments thereof. Another embodiment is directed to an expression vector comprising an isolated cDNA encoding NtMyc4 and having at least 85%, 90%, 95%, 96%, 97%, 98%, and 99% sequence identity to SEQ ID NO:3, or fragments thereof.

Another embodiment is directed to an expression vector comprising an isolated cDNA encoding NtMyc3 and having at least 85%, 90%, 95%, 96%, 97%, 98%, and 99% sequence identity to SEQ ID NO:1, or fragments thereof; and an isolated cDNA encoding NtMyc4 and having at least 85%, 90%, 95%, 96%, 97%, 98%, and 99% sequence identity to SEQ ID NO: 3, or fragments thereof.

Another embodiment is directed to an expression vector comprising cDNA encoding a Myc transcriptional factor and/or cDNA encoding a ERF transcriptional factor. In particular, this embodiment is directed to an expression vector comprising: a first sequence comprising an isolated cDNA encoding NtMyc3 and having at least 85%, 90%, 95%, 96%, 97%, 98%, and 99% sequence identity to SEQ ID NO:1, or fragments thereof; and/or a second sequence comprising an isolated cDNA encoding NtMyc4 and having at least 85%, 90%, 95%, 96%, 97%, 98%, and 99% sequence identity to SEQ ID NO:3, or fragments thereof; and an isolated cDNA encoding NtERF2 and having at least 85%, 90%, 95%, 96%, 97%, 98%, and 99% sequence identity to SEQ ID NO:5, or fragments thereof; and/or an isolated cDNA encoding NtERF5 and having at least 85%, 90%, 95%, 96%, 97%, 98%, and 99% sequence identity to SEQ ID NO:6, or fragments thereof, wherein the SEQ ID NO:5 represents the cDNA sequence encoding NtERF2, and the SEQ ID NO:6 represents the cDNA sequence encoding NtERF5.

Another embodiment is directed to a plant cell line comprising an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof.

Another embodiment is directed to a plant cell line comprising an expression vector comprising at least one ERF transcriptional factor and at least one Myc transcriptional factor. In particular, this embodiment is directed to a plant cell line comprising an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof; and an isolated cDNA encoding NtERF2 and having at least 85%, 90%, 95%, 96%, 97%, 98%, and 99% sequence identity to SEQ ID NO: 5, or fragments thereof; and/or an isolated cDNA encoding NtERF5 and having at least 85%, 90%, 95%, 96%, 97%, 98%, and 99% sequence identity to SEQ ID NO:6, or fragments thereof, wherein the SEQ ID NO:5 represents the cDNA sequence encoding NtERF2, and the SEQ ID NO:6 represents the cDNA sequence encoding NtERF5.

Another embodiment is directed to a transgenic plant comprising an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof. In a preferred embodiment, the transgenic plant is a tobacco plant.

Another embodiment is directed to a transgenic plant comprising an expression vector comprising at least one Myc transcriptional factor and at least one ERF transcriptional factor. Another embodiment is directed to a transgenic plant comprising an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof; and an isolated cDNA encoding NtERF2 and having at least 85%, 90%, 95%, 96%, 97%, 98%, and 99% sequence identity to SEQ ID NO: 5, or fragments thereof; and/or an isolated cDNA encoding NtERF5 and having at least 85%, 90%, 95%, 96%, 97%, 98%, and 99% sequence identity to SEQ ID NO:6, or fragments thereof, wherein the SEQ ID NO:5 represents the cDNA sequence encoding NtERF2, and the SEQ ID NO:6 represents the cDNA sequence encoding NtERF5. In a preferred embodiment, the transgenic plant is a tobacco plant.

Another embodiment is directed to a method for genetically regulating nicotine levels in plants, comprising introducing into a plant an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof. In a preferred embodiment, the transgenic plant is a tobacco plant.

Another embodiment is directed to a method for genetically regulating nicotine levels in plants, comprising introducing into a plant an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof; and an isolated cDNA encoding NtERF2 and having at least 85%, 90%, 95%, 96%, 97%, 98%, and 99% sequence identity to SEQ ID NO:5, or fragments thereof; and/or an isolated cDNA encoding NtERF5 and having at least 85%, 90%, 95%, 96%, 97%, 98%, and 99% sequence identity to SEQ ID NO:6, or fragments thereof, wherein the SEQ ID NO:5 represents the cDNA sequence encoding NtERF2, and the SEQ ID NO:6 represents the cDNA sequence encoding NtERF5. In a preferred embodiment, the transgenic plant is a tobacco plant. In a preferred embodiment, the nicotine level in the genetically-modified plant is increased. In another preferred embodiment, the nicotine level in the genetically-modified plant is decreased.

Various embodiments are directed to seeds derived from genetically-modified transgenic plants described herein.

Various embodiments are directed to various polynucleotide molecules that can suppress the expression levels of genes involved in the biosynthetic pathways for the production of alkaloids, flavonoids, and nicotine. Examples of suitable compositions include ERF and Myc anti-sense polynucleotides that are complementary to ERF and Myc transcript sequences, such as RNAi molecules, microRNAs, and other dominant negative constructs known to persons skilled in the art.

It will be appreciated that, although specific embodiments of the invention have been described herein for purposes of illustration, various modifications may be made without departing from the spirit and scope of the invention. Accordingly, the invention is not limited except as by the appended claims.

We claim:

1. An expression vector comprising a heterologous promoter operably linked to a nucleic acid molecule comprising a nucleic acid sequence at least 95% identical to SEQ ID NO: 1.

2. The expression vector of claim 1, wherein the heterologous promoter is a constitutively active promoter.

3. The expression vector of claim 1, wherein the heterologous promoter is an inducible promoter.

4. The expression vector of claim 1, wherein the nucleic acid molecule comprises a nucleic acid sequence at least 96% identical to SEQ ID NO: 1.

5. The expression vector of claim 1, wherein the nucleic acid molecule comprises a nucleic acid sequence at least 97% identical to SEQ ID NO: 1.

6. The expression vector of claim 1, wherein the nucleic acid molecule comprises a nucleic acid sequence at least 98% identical to SEQ ID NO: 1.

7. The expression vector of claim 1, wherein the nucleic acid molecule comprises a nucleic acid sequence at least 99% identical to SEQ ID NO: 1.

8. The expression vector of claim 1, wherein the nucleic acid molecule comprises a nucleic acid sequence 100% identical to SEQ ID NO: 1.

9. The expression vector of claim 1, wherein the nucleic acid molecule encodes the amino acid sequence of SEQ ID NO: 2.

10. A tobacco plant or tobacco seed comprising an expression vector comprising a heterologous promoter operably linked to a nucleic acid molecule comprising a nucleic acid sequence at least 95% identical to SEQ ID NO: 1.

11. The tobacco plant or tobacco seed of claim 10, wherein the tobacco plant or tobacco seed is a *Nicotiana tabacum* plant or a *Nicotiana tabacum* seed.

12. The tobacco plant or tobacco seed of claim 10, wherein the heterologous promoter is a constitutively active promoter.

13. The tobacco plant or tobacco seed of claim 10, wherein the heterologous promoter is an inducible promoter.

14. The tobacco plant or tobacco seed of claim 10, wherein the nucleic acid molecule comprises a nucleic acid sequence at least 96% identical to SEQ ID NO: 1.

15. The tobacco plant or tobacco seed of claim 10, wherein the nucleic acid molecule comprises a nucleic acid sequence at least 97% identical to SEQ ID NO: 1.

16. The tobacco plant or tobacco seed of claim 10, wherein the nucleic acid molecule comprises a nucleic acid sequence at least 98% identical to SEQ ID NO: 1.

17. The tobacco plant or tobacco seed of claim 10, wherein the nucleic acid molecule comprises a nucleic acid sequence at least 99% identical to SEQ ID NO: 1.

18. The tobacco plant or tobacco seed of claim 10, wherein the nucleic acid molecule comprises a nucleic acid sequence 100% identical to SEQ ID NO: 1.

19. The tobacco plant or tobacco seed of claim 10, wherein the nucleic acid molecule encodes the amino acid sequence of SEQ ID NO: 2.

* * * * *

SEQUENCE LISTING

```
Sequence total quantity: 10
SEQ ID NO: 1            moltype = DNA  length = 2040
FEATURE                 Location/Qualifiers
source                  1..2040
                        mol_type = other DNA
                        organism = Nicotiana tabacum
SEQUENCE: 1
atgactgatt acagcttacc caccatgaat ttgtggaata ctagtggtac taccgatgac  60
aacgtttcta tgatggaatc ttttatgtct tctgatctca cttcattttg ggctacttct  120
aattctacta ctgctgctgt tacctctaat tctaatctta ttccagttaa taccctaact  180
gttcttcttc cgtcttcttg tgcttctact gtcacagctg tggctgtcga tgcttcaaaa  240
tccatgtctt ttttcaacca agaaactctt cagcagcgtc ttcaaaccct cattgatggt  300
gctcgtgaga cgtggaccta tgccatcttt tggcagtcat ccgtcgttga tttatcgagt  360
ccgtttgtgt tgggctgggg agatggttac tacaaaggtg aagaagataa agccaatagg  420
aaattagctg tttcttctcc tgcttatatt gctgagcaag aacaccgaaa aaaggttctc  480
cgggagctga attcgttgat ctccggcacg caaaccggca ctgatgatgc cgtcgatgaa  540
gaagttaccg acactgaatg gttcttcctt atttccatga cccaatcgtt tgttaacgga  600
agtgggcttc cgggtcaggc cttatacaat tccagcccta tttgggtcgc cggagcagag  660
aaattggcag cttcccactg cgaacgggct cggcaggccc agggattcgg gcttcagacg  720
atggtttgta ttccttcagc aaacggcgtg gttgaattgg gctccacgga gttgataatc  780
cagagttgtg atctcatgaa caaggttaga gtattgttta acttcaataa tgatttgggc  840
tctggttcgt gggctgtgca gcccgagagc gatccgtccg ctctttggct cactgatcca  900
tcgtctgcag ctgtagaagt ccaagattta aatacagtta aggcaaattc agttccatca  960
agtaatagta gtaagcaagt tgtgtttgat aatgagaata atggtcacag ttctgataat  1020
cagcaacagc agcattctaa gcatgaaaca caaggatttt tcacaaggga gttgaatttt  1080
tcagaatttg ggtttgatgg aagtagtaat aataggaatg ggaattcatc actttcttgc  1140
aagccagagt cgggggaaat cttgaatttt ggtgatagta ctaagaaaag tgcaaatggg  1200
aacttatttt cgggtcagtc ccattttggg gcaggggagg agaataagaa caagaaaagg  1260
tcacctgctt ccagaggaag caatgaagaa ggaatgcttt catttgtttc gggtacaatc  1320
ttgcctgcag cttctggtgc gatgaagtca agtggaggtg taggtgaaga ctctgatcat  1380
tcggatcttg aggcctcagt ggtgaaagaa gctgaaagta gtagagttgt agaacccgaa  1440
aagaggccaa agaagcgagg aaggaagcca gcaaatggac gggaggaacc tttgaatcac  1500
gtcgaagcag agaggcaaag gagagagaaa ttaaaccaaa ggttctacgc attaagagct  1560
gttgttccga atgtgtccaa gatggacaag gcatcactgc ttggagatgc aatttcatat  1620
attaatgagc tgaagttgaa gcttcaaaat acagaaacag atagagaaga attgaagagc  1680
caaatagaag atttaaagaa agaattagtt agtaaagact caaggcgccc tggtcctcca  1740
ccatcaaatc atgatcacaa gatgtctagc catactggaa gcaagattgt agacgtggat  1800
atagatgtta agataattgg atgggatgcg atgattcgta tacaatgtaa taaaaagaat  1860
catccagctg caaggttaat ggtagccctc aaggagttag atctagatgt gcaccatgcc  1920
agtgtttcag tggtgaacga tttgatgatc caacaagcca ctgtgaaaat gggtagcaga  1980
ctttacacgg aagagcaact taggatagca ttgacatcca gagttgctga aacacgctaa  2040

SEQ ID NO: 2            moltype = AA  length = 679
FEATURE                 Location/Qualifiers
source                  1..679
                        mol_type = protein
                        organism = Nicotiana tabacum
SEQUENCE: 2
MTDYSLPTMN LWNTSGTTDD NVSMMESFMS SDLTSFWATS NSTTAAVTSN SNLIPVNTLT  60
VLLPSSCAST VTAVAVDASK SMSFFNQETL QQRLQTLIDG ARETWTYAIF WQSSVVDLSS  120
PFVLGWGDGY YKGEEDKANR KLAVSSPAYI AEQEHRKKVL RELNSLISGT QTGTDDAVDE  180
EVTDTEWFFL ISMTQSFVNG SGLPGQALYN SSPIWVAGAE KLAASHCERA RQAQGFGLQT  240
MVCIPSANGV VELGSTELII QSCDLMNKVR VLFNFNNDLG SGSWAVQPES DPSALWLTDP  300
SSAAVEVQDL NTVKANSVPS SNSSKQVVFD NENNGHSSDN QQQQHSKHET QGFFTRELNF  360
SEFGFDGSSN NRNGNSSLSC KPESGEILNF GDSTKKSANG NLFSGQSHFG AGEENKNKKR  420
SPASRGSNEE GMLSFVSGTI LPAASGAMKS SGGVGEDSDH SDLEASVVKE AESSRVVEPE  480
KRPKKRGRKP ANGREEPLNH VEAERQRREK LNQRFYALRA VVPNVSKMDK ASLLGDAISY  540
INELKLKLQN TETDREELKS QIEDLKKELV SKDSRRPGPP PSNHDHKMSS HTGSKIVDVD  600
IDVKIIGWDA MIRIQCNKKN HPAARLMVAL KELDLDVHHA SVSVVNDLMI QQATVKMGSR  660
LYTEEQLRIA LTSRVAETR                                              679

SEQ ID NO: 3            moltype = DNA  length = 2046
FEATURE                 Location/Qualifiers
source                  1..2046
```

```
                        mol_type = other DNA
                        organism = Nicotiana tabacum
SEQUENCE: 3
atgactgatt acagcttacc caccatgaat ttgtggaata ctagtggtac taccgatgac  60
aacgttacta tgatggaagc ttttatgtct tctgatctca cttcattttg ggctacttct  120
aattctactg ctgttgctgc tgttacctct aattctaatc atattccagt taatacccca  180
acggttcttc ttccgtcttc ttgtgcctct actgtcacag ctgtggctgt cgatgcttca  240
aaatccatgt ctttttcaa ccaagaaacc cttcaacagc gtcttcaaac gctcattgat  300
ggtgctcgtg agacgtggac ctatgccatc ttttggcagt catccgccgt tgatttaacg  360
agtccgtttg tgttgggctg gggagatggt tactacaaag gtgaagaaga taaagccaat  420
aggaaattag ctgtttcttc tcctgcttat atagctgagc aagaacaccg gaaaaaggtt  480
ctccgggagc tgaattcgtt gatttccggc acgcaaaccg gcactgatga tgccgtcgat  540
gaagaagtta ccgacactga atggttcttc cttatttcca tgacccagtc gtttgttaac  600
ggaagtgggc ttccgggtca ggccttatac aattccagcc ctatttgggt cgccggagca  660
gagaaattgg cagcttccca ctgcgaacgg gctcggcagg cccagggatt cgggcttcag  720
acgatggttt gtattccttc agcaaacggc gtggttgaat tgggctccac ggagttgatt  780
attcagagtt ctgatctcat gaacaaggtt agagtattgt ttaacttcaa taatgatttg  840
ggctctggtt cgtgggctgt gcaacccgag agcgatccgt ccgctctttg gctcactgat  900
ccatcgtctg cagctgtaca agtcaaagat ttaaatacag ttgaggcaaa ttcagttcca  960
tcaagtaata gtagtaagca agttgtattt gataatgaga ataatggtca cagttgtgat  1020
aatcagcaac agcaccattc tcggcaacaa acacaaggat tttttacaag ggagttgaac  1080
ttttcagaat tcgggtttga tggaagtagt aataatagga atgggaattc atcactttct  1140
tgcaagccag agtcgggga aatcttgaat tttggtgata gcactaagaa aagtgcaaat  1200
gggaacttat ttccggtca gtctcatttt ggtgcagggg aggagaataa gaagaagaaa  1260
aggtcacctg cttccagagg aagcaatgaa gaaggaatgc tttcatttgt ttcaggtaca  1320
atcttgcctg cagcttctgg tgcgatgaag tcaagtggat gtgtcggtga agactcctct  1380
gatcattcgg atcttgaggc ctcagtggtg aaagaagctg aaagtagtag agttgtagaa  1440
cccgaaaaga ggccaaagaa gcgaggaagg aagccagcaa atggacgtga ggaacctttg  1500
aatcacgtcg aagcagagag gcaaaggaga gagaaattaa accaaaggtt ctacgcttta  1560
agagctgttg ttccgaatgt gtccaagatg gacaaggcat cactgcttgg agatgcaatt  1620
tcatatatta atgagctgaa gttgaagctt caaactacag aaacagatag agaagacttg  1680
aagagccaaa tagaagattt gaagaaagaa ttagatagta aagactcaag gcgccctggt  1740
cctccaccac caaatcaaga tcacaagatg tctagccata ctggaagcaa gattgtagat  1800
gtggatatag atgttaagat aattggatgg gatgcgatga ttcgtataca atgtaataaa  1860
aagaaccatc cagctgcaag gttaatggta gccctcaagg agttagatct agatgtgcac  1920
catgccagtg tttcagtggt gaatgatttg atgatccaac aagccacagt gaaaatgggt  1980
agcagacttt acacggaaga gcaacttagg atagcattga catccagagt tgctgaaaca  2040
cgctaa                                                            2046

SEQ ID NO: 4            moltype = AA  length = 681
FEATURE                 Location/Qualifiers
source                  1..681
                        mol_type = protein
                        organism = Nicotiana tabacum
SEQUENCE: 4
MTDYSLPTMN LWNTSGTTDD NVTMMEAFMS SDLTSFWATS NSTAVAAVTS NSNHIPVNTP  60
TVLLPSSCAS TVTAVAVDAS KSMSFFNQET LQQRLQTLID GARETWTYAI FWQSSAVDLT  120
SPFVLGWGDG YYKGEEDKAN RKLAVSSPAY IAEQEHRKKV LRELNSLISG TQTGTDDAVD  180
EEVTDTEWFF LISMTQSFVN GSGLPGQALY NSSPIWVAGA EKLAASHCER ARQAQGFGLQ  240
TMVCIPSANG VVELGSTELI IQSSDLMNKV RVLFNFNNDL GSGSWAVQPE SDPSALWLTD  300
PSSAAVQVKD LNTVEANSVP SSNSSKQVVF DNENNGHSCD NQQQHHSRQQ TQGFFTRELN  360
FSEFGFDGSS NNRNGNSSLS CKPESGEILN FGDSTKKSAN GNLFSGQSHF GAGEENKKKK  420
RSPASRGSNE EGMLSFVSGT ILPAASGAMK SSGCVGEDSS DHSDLEASVV KEAESSRVVE  480
PEKRPKKRGR KPANGREEPL NHVEAERQRR EKLNQRFYAL RAVVPNVSKM DKASLLGDAI  540
SYINELKLKL QTTETDREDL KSQIEDLKKE LDSKDSRRPG PPPPNQDHKM SSHTGSKIVD  600
VDIDVKIIGW DAMIRIQCNK KNHPAARLMV ALKELDLDVH HASVSVVNDL MIQQATVKMG  660
SRLYTEEQLR IALTSRVAET R                                           681

SEQ ID NO: 5            moltype = DNA  length = 702
FEATURE                 Location/Qualifiers
misc_feature            1..702
                        note = cDNA sequence of NtERF2
source                  1..702
                        mol_type = other DNA
                        organism = synthetic construct
SEQUENCE: 5
atgtatcaac caatttcgac cgagctacct ccgacgagtt tcagtagtct catgccatgt  60
ttgacggata catggggtga cttgccgtta aaagttgatg attccgaaga tatggtaatt  120
tatgggctct taagtgacgc tttaactgcc ggatggacgc cgtttaattt aacgtccacc  180
gaaataaaag ccgagccgag ggaggagatt gagccagcta cgattcctgt tccttcagtg  240
gctccacctg cggagactac gacggctcaa gccgttgttc ccaaggggag gcattatagg  300
ggcgttaggc aaaggccgtg gggaaattt gcggcggaaa taagggaccc agctaaaaac  360
ggcgcacggg tttggctagg gacttatgag acggctgaag aagccgcgct cgcttatgat  420
aaagcagctt acaggatgcg cggctccaag gctctattga attttccgca taggatcggc  480
ttaaatgagc ctgaaccggt tagactaacc gctaagagac gatcacctga accggctagc  540
tcgtcaatat catcggcttt ggaaaatggc tcgccgaaac ggaggagaaa agctgtagcg  600
gctaagaagg ctgaattaga agtgcaaagc cgatcaaatg ctatgcaagt tgggtgccag  660
atggaacaat ttccagttgg cgagcagcta ttagtcagtt aa                    702
```

-continued

```
SEQ ID NO: 6            moltype = DNA  length = 705
FEATURE                 Location/Qualifiers
misc_feature            1..705
                        note = NtERF5 cDNA
source                  1..705
                        mol_type = other DNA
                        organism = synthetic construct
SEQUENCE: 6
atgtcaagta actcaagccc actagaaata gacacttcat tttcacattc caacttcttc  60
tttctccaag atcaatcacc aattttacaa tgggatgatg atcttttctt caatgatcca  120
tggtttgatg atgatcaatc accaattata ccatgtaact cagagaaaga tgaaaatcat  180
caagtatttg aagaatcctc agacaataca atcatgtcaa aaggaagtag ccatggtcaa  240
gaattagaag aggtaacatc ccaagaagaa aaagaaaaag aagaagaaga aaaacactat  300
ataggagtta gaaaaaggcc atggggtaaa tatgcagcag aaataagaga ttcaacaaga  360
aatggaatta gggtttggtt agggacattt gatacagctg aagaagctgc tttagcttat  420
gatcaagctg cattatcgat gagaggtcct tggtctcttc ttaattttcc attggagaaa  480
gtcaagaaat cacttgaaaa aattgagtat tcttgtaaag atggattgtc tcctgctgct  540
gttctaaaag ctactcataa aacaaggaga gtgaagcata aaagaagtag tagaaagaaa  600
aagaataaag aaactcataa tgttattgtt tttgaggact tgggtgctga gttattagaa  660
gagcttttaa tgacttcatc acaacattcg tgtcgaaggg actga                 705

SEQ ID NO: 7            moltype = DNA  length = 57
FEATURE                 Location/Qualifiers
misc_feature            1..57
                        note = NtPMT1a promoter
source                  1..57
                        mol_type = other DNA
                        organism = synthetic construct
SEQUENCE: 7
ctgcacgttg taatgaattt ttaactatta tattatatcg agttgcgccc tccactc     57

SEQ ID NO: 8            moltype = DNA  length = 57
FEATURE                 Location/Qualifiers
misc_feature            1..57
                        note = Synthesized
source                  1..57
                        mol_type = other DNA
                        organism = synthetic construct
SEQUENCE: 8
cttctttttt atatctaaaa taaagataat aaaatattcg attttctccc tccactc     57

SEQ ID NO: 9            moltype = DNA  length = 14
FEATURE                 Location/Qualifiers
misc_feature            1..14
                        note = G-Box
source                  1..14
                        mol_type = other DNA
                        organism = synthetic construct
SEQUENCE: 9
ctgcacgttg taat                                                    14

SEQ ID NO: 10           moltype = DNA  length = 14
FEATURE                 Location/Qualifiers
misc_feature            1..14
                        note = Mutant G-Box
source                  1..14
                        mol_type = other DNA
                        organism = synthetic construct
SEQUENCE: 10
ctgcttaatg taat                                                    14
```